| United States Patent [19] | [11] 4,028,467 |
|---|---|
| Berger | [45] * June 7, 1977 |

[54] ANALGESIC COMPOSITIONS COMPRISING LEVO-PROPOXYPHENE AND BENZO DIAZEPINE AND PROCESS

[76] Inventor: Frank M. Berger, 190 E. 72nd St., New York, N.Y. 10021

[ * ] Notice: The portion of the term of this patent subsequent to Apr. 12, 1994, has been disclaimed.

[22] Filed: June 12, 1975

[21] Appl. No.: 586,329

Related U.S. Application Data

[63] Continuation-in-part of Ser. No. 541,968, Jan. 17, 1975, abandoned, which is a continuation-in-part of Ser. No. 463,350, April 23, 1974, abandoned.

[52] U.S. Cl. .................. 424/244; 424/308; 424/311
[51] Int. Cl.² ............... A61K 31/22; A61K 31/33; A61K 31/235
[58] Field of Search .................. 424/308, 244, 311

[56] References Cited

UNITED STATES PATENTS 3,845,192  10/1974  Miller ............................. 424/308

OTHER PUBLICATIONS

Drugs of Choice 1974–1975, Modell, pp. 405–406.
The Pharmacological Bases of Therapeutics, pp. 278–279 & pp. 187–191.
U.S. Dispensatory 26th Ed. pp. 962–964.

*Primary Examiner*—Stanley J. Friedman

[57] ABSTRACT

Analgesic compositions having a remarkably high analgesic activity and a process for obtaining an analgesic effect are provided, in which the active components are levopropoxyphene and a benzodiazepine. The analgesic activity of these combinations is remarkable, inasmuch as neither levopropoxyphene nor benzodiazepines when administered separately display analgesic activity.

17 Claims, No Drawings

ANALGESIC COMPOSITIONS COMPRISING LEVO-PROPOXYPHENE AND BENZO DIAZEPINE AND PROCESS

This application is a continuation-in-part of Ser. No. 541,968, filed Jan. 17, 1975, now abandoned, the subject matter of which is carried forward in Ser. No. 665,595, filed Mar. 10, 1976. Ser. No. 541,968 is in turn a continuation-in-part of Ser. No. 463,350, filed Apr. 23, 1974, also now abandoned.

Propoxyphene, 4-dimethylamino-3-methyl-1,2-diphenylpropionooxybutane is related structurally to methadone, and has the formula

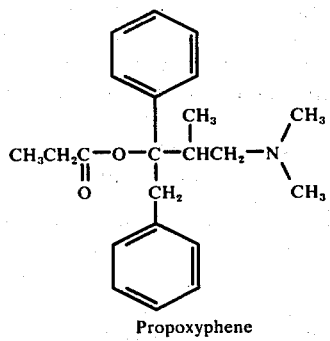

Propoxyphene

The compound exists as four stereoisomers.

The less soluble diastereoisomer is designated as the $\alpha$-isomer, and the more soluble as the $\beta$-isomer. The $\alpha$, d, 1-and$\alpha$,-d-diasterioisomers have marked analgesic activity. The $\alpha$,-1-diastereoisomer has no analgesic action, but it has antitussive activity. The $\beta$-diastereoisomers are substantially inactive. The *United States Dispensatory*, 26th Edition, page 963, indicates that the $\alpha$, dextro isomer, $\alpha$, d-propoxyphene hydrochloride, is as effective in humans as codeine phosphate in relieving pain. On the other hand, the $\alpha$-,-d,1-racemate has about one-half the analgesic potency of codeine, due no doubt to the presence in an amount of 50% by weight of the analgesically-inactive $\alpha$, laevo isomer. Regarding the $\alpha$, laevo isomer, The *United States Dispensatory* states that, in contrast to propoxyphene, 1-propoxyphene has therapeutically useful antitussive activity but no analgesic action.

$\alpha$,-d-propoxyphene has little, if any, addicting liability, and is used to provide relief in mild to moderate pain, whether acute, chronic, or recurrent. It tends to produce fewer gastrointestinal side effects than codeine, but is not sufficiently potent to relieve severe pain, and it is of little utility as an antitussive. Several formulations of $\alpha$, d-propoxyphene hydrochloride are available commercially.

Goodman and Gilman, The *Pharmaceutical Basis of Therapeutics*, 3rd Edition, indicate that $\alpha$, d-propoxyphene produces analgesia by acting on the central nervous system. Oral doses of the order of 65 to 100 mg. are about as effective as oral doses of 65 mg. of codeine. Lower doses, 32 mg., for example, are sometimes no more effective than a placebo, however.

Because of its relatively low activity, except at rather high doses, $\alpha$, d-propoxyphene has been the subject of investigation, with the view of improving its effectiveness.

Miller, U.S. Pat. No. 3,845,192, patented Oct. 29, 1974, reported that the addition of one or both of the tranquilizers chlordiazepoxide and diazepam to $\alpha$, d-propoxyphene even at doses below those at which these benzodiazepines exhibit tranquilizing effects results in improved analgesia, notably a higher pain threshold. No other benzodiazepines are referred to.

Miller, U.S. Pat. No. 3,749,797, patented July 31, 1973 suggested combinations of $\alpha$, d-propoxyphene and namoxyrate, and No. 3,800,041 suggested combinations of $\alpha$, d-propoxyphene and indomethacin, each of which give an enhanced analgesic effect.

In all of these combinations, at least one component, and in the case of the two-mentioned patents, both to the components, are analgesics.

In accordance with the instant invention, it has now been determined that combinations of levopropoxyphene, the non-analgesic stereoisomer of $\alpha$, d-propoxyphene, in combination with one or more benzodiazepines displays an analgesic activity no less great than that of similar combinations of $\alpha$, d-propoxyphene with chlorodiazepoxide or diazepam, the combinations of U.S. Pat. No. 3,845,192. That such combinations have analgesic activity is quite remarkable, in view of the lack of analgesic activity of either component. While it might be expected that combinations containing $\alpha$, d-propoxyphene would have at least the analgesic activity of $\alpha$, d-propoxyphene, it would not be expected that combinations containing the levopropoxyphene would have any analgesic activity whatsoever, inasmuch as levopropoxyphene is not an analgesic, and the benzodiazepines are not analgesics, either, but tranquilizers.

The benzodiazepines of which at least one and optionally two, three or more can be employed in combinations with levopropoxyphene are defined by the formula:

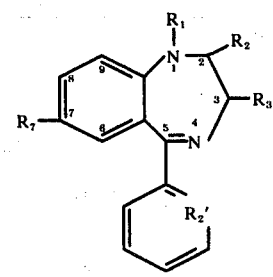

In the above formula, the R substituents are defined as follows:

$R_1$ is selected from the group consisting of hydrogen

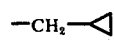

alkyl, and amino or alkylamino of the type

in which R and R' are selected from the group consisting of hydrogen, lower alkyl having from one to three carbon atoms, and bivalent alkylene having from two to four carbon atoms; and linked to the nitrogen at two positions to form a heterocyclic ring;

$R_2$ is selected from the group consisting of hydrogen, oxo oxygen =O, hydroxyl OH, alkyl, and amino or alkylamino of the type

where R and R' are as defined above;

$R_3$ is selected from the group consisting of hydrogen, hydroxyl OH and carboxyl COOH;

$R_7$ is selected from the group consisting of hydrogen, halogen and nitro $NO_2$, the halogen being, for example, chlorine, or bromine;

$R_2'$ is selected from the group consisting of

where X is halogen,

and amino or alkylamino

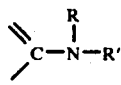

where R and R' are as defined above.

Representative benzodiazepines falling within the above formula which can be employed include

|  | $R_1$ | $R_2$ | $R_3$ | $R_7$ | $R_2'$ |
|---|---|---|---|---|---|
| Chlordiazepoxide | H | $NHCH_3$ | H | Cl | >CH |
| Diazepam | $CH_3$ | =O | H | Cl | >CH |
| Oxazepam | H | =O | OH | Cl | >CH |
| Clorazepate | H | $(OH_2)$ | COOH | Cl | >CH |
| Flurazepam | —$CH_2CH_2$—N($C_2H_5$)$C_2H_5$ | =O | H | Cl | >CF |
| Lorazepam | H | =O | OH | Cl | >CCl |
| Nitrazepam | H | =O | H | $NO_2$ | >CH |
| Medazepam | $CH_3$ | H | H | Cl | >CH |
| Bromazepam | H | =O | H | Br | >N |
| Prazepam | —$CH_2$—◁ | =O | H | Cl | >CH |

The levopropoxyphene and benzodiazepine can be employed as the free base or as their pharmaceutically acceptable salts. A pharmaceutically acceptable salt is a salt whose toxicity is not significantly greater than that of the free base. Pharmaceutically acceptable salts are readily prepared by reaction of the free amine with an organic or inorganic acid providing a pharmaceutically acceptable anion. Any pharmaceutically acceptable salt can be used including, for example, the hydrochloride, hydrobromide, sulphate, bisulphate, acetate, salicylate, valerate, oleate, laurate, borate, benzoate, lactate, phosphate, tosylate, citrate, maleate, fumarate, succinate, tartrate, and napsylate. Usually, the levopropoxyphene is employed as the hydrochloride or napsylate salt, and the benzodiazepine is normally employed as the hydrochloride.

In the combinations of the invention, the leveopropoxyphene gives an effective analgesic effect in a single oral dose providing an amount within the range from about 0.5 to about 30 mg. levopropoxyphene per kg. of animal body weight. The doses can, of course, be varied according to the species of animal treated, the particular state which is treated, the route of administration, and other factors, as is well known. If the species is a sensitive one, a lesser oral dose will suffice, such as, for a single oral dose, an amount of levopropoxyphene within the range from about 0.5 to about 5 mg. per kg. of animal body weight. In parenteral administration, the doses are lower by a factor of one-third to one-fifth of the amount of the oral doses. For medical applications, it is suggested that reference be made to *The Physician's Desk Reference To Pharmaceutical Specialties and Biologicals*, 27th Edition (1973) Medical Economics, Inc., page 875.

The benzodiazepine is used in an amount to impart analgesic activity to the nonanalgesic levopropoxyphene, which amount accordingly constitutes a potentiating dose. The potentiating dose varies with the benzodiazepine, and also varies with the species of animal, the veterinary or medical state being treated, the route of administration, and other known factors.

Generally, an analgesic effect is obtained by employing any of the benzodiazepines in the normal dosage amounts for the particular diazepine employed when used as a tranquilizer. The transquilizing dosage amounts for benzodiazepines are set forth in The *Physician's Desk Reference of Pharmaceutical Specialties and Biologicals*, 27th Edition, (1973), Medical Economics, Inc., pages 537, 1169, 1178, 1192 and 1567 or in similar publications such as *Martindale, The Extra Pharmacopoeia, The Pharmaceutical Press*, London, 26th Edition, (1972). Lesser doses can, however, be used provided only that the relative proportions of benzodiazepine and levopropoxyphene in the combinations of the invention are selected to give an analgesic effect. The relative proportions depend, of course, upon the particular benzodiazepine employed, the animal, the veterinary or medical state being treated, the route of administration, and other known factors. In general, however, the weight ratio of levopropoxyphene-benzodiazepine is within the range from 100:0.5 to 2:1.

The compositions in accordance with the invention are nonaddictive, and consequently administration of the compositions can be repeated intermittently or recurringly, on a regular or irregular basis, as required.

The process in accordance with the invention accordingly comprises administering to a warm-blooded animal both levopropoxyphene and a benzodiazepine, separately, i.e., in succession, or together, in amounts to give an analgesic effect when present together in the animal. In general, the compositions are conveniently administered and accordingly are usually formulated in combination with inert adjuvants appropriate for the particular combination and route of administration that is selected.

The preferred route of administration is orally. The compositions for oral administration can assume any of the normal forms, such as tablets, capsules, suspensions, elixirs, powders and jellies. The compositions can also be administered parenterally, such as by intramuscular, intravenous or subcutaneous administration, using conventional procedures, or in the form of rectal suppositories.

In combinations with adjuvants and inert diluents, the compositions of the invention can have any desired concentration of the active ingredients, i.e., the levopropoxyphene and the benzodiazepine. A more concentrated composition can be formulated for dilution with water or other inert liquid before use. Usually, however, it is convenient to have the composition available in unit dose form, i.e., a unit dosage amount such that one portion of the composition provides the normally desired dose. Larger doses can be obtained by combining units, and lesser doses by subdividing units, facilitated by score lines or demarcations of some conventional sort.

The compositions of the invention can also include additional active ingredients to bolster or supplement the analgesic effect, including, for example, aspirin, acetysalicylic acid, acetylphenetadine, acetylaminophene, codeine, and similer components.

In accord with usual medical practice, the combinations in accordance with the invention can be supplied in unit dose compositions comprising from about 25 to about 200 mg. of the levopropoxyphene (calculated as the free base) and from about 0.5 to about 25 mg. of the benzodiazepine or benzodizepines (calculated as the free base).

In the following Examples, the compositions in accordance with the invention were evaluated using a standardized "hot plate" test for analgesia as described by Nathan B. Eddy and Dorothy Lineback, *The Journal of Pharmacological and Experimental Therapy* 107 385 (1953). It is generally accepted that this test measures analgesic action and that the results obtained in this test are applicable to all kinds of warm-blooded animals including man. The results of the test can be extrapolated to humans in a relative or qualitative but not in a quantitative manner.

The test is carried out by placing mice onto a hot plate, the temperature of which is maintained between 55° and 55.5° C, and determining the reaction time of the test animal to the sensation of heat, evidenced by lifting the front feet and kicking the hind feet. Normal average reaction time for mice prior to administration of the analgesic composition in accordance with the invention is 9.51±1.02 seconds, with more than 90% of the mice falling within the range from 6 to 13 seconds. The lengthening of the reaction time at a given interval following the administration of a substance is a measure of the analgesic effect. No mouse is left on the hot plate for longer than 30 seconds, since injury might result; failure to react in 30 seconds is thus reported as complete analgesia.

In the standardized test, the reaction time of the mice is noted at 10 minute intervals for one hour following administration of the analgesic composition being evaluated. However, in the present Examples, the tabulated data in Table I gives only the results at 30 minutes and at 60 minutes following administration. Administration in each case was intraperitoneally. The test dosage is shown in the Table.

EXAMPLES 1 to 14

A number of combinations were made up composed of levopropoxyphene and the benzodiazepine named in Table I. In some cases, a number of dosages were used, while in others, only one dosage was used.

The results of the test were as follows:

TABLE I

| Example No. | Compound | Dose (mg/kg) | Number of Mice | Reaction Time at 30 min. after administration | Reaction Time at 60 min. after administration | Number With Complete Analgesia at 30 min. after administration | Number With Complete Analgesia at 60 min. after administration |
|---|---|---|---|---|---|---|---|
| Control A | | Untreated | 32 | 10.7 | 10.5 | 0 | 0 |
| Control B1 | Levopropoxyphene (Novrad) | 25 | 16 | 9.2 | 8.9 | 0 | 0 |
| B2 | | 40 | 24 | 12.5 | 11.6 | 1 | 1 |
| B3 | | 50 | 16 | 11.3 | 11.2 | 0 | 0 |
| B4 | | 60 | 8 | 19.5 | 8.3 | 2 | 0 |
| B5 | | 80 | 8[1] | | | | |
| B6 | | 100 | 8[2] | | | | |
| Control C | Chlordiazepoxide (Librium) | 50 | 8 | 14.2 | 11.7 | 0 | 0 |
| 1 | Levopropoxyphene (Novrad) | 25 | | | | | |
| | Chlordiazepoxide (Librium) | 50 | 16 | 20.4 | 22.5 | 5 | 6 |
| 2 | Levopropoxyphene (Novrad) | 50 | | | | | |
| | Chlordiazepoxide (Librium) | 50 | 16 | 25.6 | 20.9 | 8 | 5 |
| 3 | Levopropoxyphene (Novrad) | 60 | | | | | |
| | Chlordiazepoxide (Librium) | 50 | 16 | 27.1 | 28.1 | 11 | 13 |
| Control D | Diazepam (Valium) | 25 | 8 | 18.1 | 16.9 | 0 | 0 |
| 4 | Levopropoxyphene (Novrad) | 25 | | | | | |
| | Diazepam (Valium) | 25 | 24 | 29.1 | 23.1 | 12 | 8 |
| 5 | Levopropoxyphene (Novrad) | 40 | | | | | |
| | Diazepam (Valium) | 25 | 16 | 21.3 | 23.4 | 4 | 8 |
| Control E 1 | Oxazepam (Serax) | 25 | 8 | 10.7 | 10.8 | 0 | 0 |
| 6 | Levopropoxyphene (Novrad) | 25 | | | | | |
| | Oxazepam (Serax) | 25 | 8 | 27.6 | 29.4 | 5 | 7 |

TABLE I-continued

| Example No. | Compound | Dose (mg/kg) | Number of Mice | Reaction Time at 30 min. after administration | Reaction Time at 60 min. after administration | Number With Complete Analgesia at 30 min. after administration | Number With Complete Analgesia at 60 min. after administration |
|---|---|---|---|---|---|---|---|
| Control E 2 | Oxazepam (Serax) | 50 | 8 | 16.5 | 18.7 | 1 | 0 |
| 7 | Levopropoxyphene (Novrad) | 25 | | | | | |
| | Oxazepam (Serax) | 50 | 8 | 27.3 | 25.2 | 4 | 4 |
| 8 | Levopropoxyphene (Novrad) | 50 | | | | | |
| | Oxazepam (Serax) | 50 | 8 | 27.1 | 27.6 | 4 | 6 |
| Control F | Flurazepam (Dalmane) | 50 | 8 | 15.4 | 13.7 | 0 | 0 |
| 9 | Levopropoxyphene (Novrad) | 25 | | | | | |
| | Flurazepam (Dalmane) | 50 | 8 | 22.1 | 17.8 | 4 | 1 |
| 10 | Levopropoxyphene (Novrad) | 40 | | | | | |
| | Flurazepam (Dalmane) | 25 | 8 | 25.8 | 26.4 | 5 | 3 |
| 11 | Levopropoxyphene (Novrad) | 40 | | | | | |
| | Flurazepam (Dalmane) | 50 | 8 | 28.2 | 29.4 | 6 | 6 |
| Control G 1 | Clorazepate (Tranxene) | 50 | 8 | 16.9 | 15.6 | 1 | 1 |
| 12 | Levopropoxyphene (Novrad) | 50 | | | | | |
| | Clorazepate (Tranxene) | 50 | 8 | 26.8 | 23.6 | 5 | 4 |
| Control G 2 | Clorazepate (Tranxene) | 100 | 8 | 14.4 | 16.5 | 2 | 0 |
| 13 | Levopropoxyphene (Novrad) | 50 | | | | | |
| | Clorazepate (Tranxene) | 100 | 8 | 26.0 | 27.7 | 4 | 7 |
| Control H | Lorazepam (Tavor) | 50 | 8 | 18.9 | 13.2 | 3 | 1 |
| 14 | Levopropoxyphene (Novrad) | 50 | | | | | |
| | Lorazepam (Tavor) | 50 | 8 | 25.7 | 23.5 | 6 | 5 |

[1] Two deaths  
[2] 8 deaths  
showing dosage too high

It is apparent from Controls B5 and B6 that at dosages in excess of 60 mg. per kg. the toxicity limit of the levopropoxyphene is exceeded. Consequently, the maximum dose used in these tests with mice was 60 mg. per kg.

It is also apparent from the untreated Control A and the Controls B1-B4 that levopropoxyphene is not effective as an analgesic by itself. Some of the benzodiazepines in Controls C to H evidence a minimal effect, but in no way as great an analgesic effect as for the combinations of Examples 1 to 14. The data show true synergism, which is all the more remarkable because neither of these components, taken separately, displays analgesic properties.

The following are Examples of compositions for dosage units or other application forms in accordance with the invention:

Tablet formulation

| | Parts/tablet |
|---|---|
| Active compounds | 15 |
| Lactose | 86 |
| Corn starch (dried) | 45.5 |
| Gelatin | 2.5 |
| Magnesium stearate | 1.0 |

The compound was powdered and passed through a sieve, and well mixed with the lactose and 30 mg. of the corn starch.

The mixed powders were combined with a warm gelatin solution prepared by stirring the gelatin in water and heating to form a 10% w./w. solution, granulated by passing through a B.S. No. 12 sieve, and the moist granules dried at 40° C.

The dried granules were re-granulated and the balance of the starch and the magnesium stearate were added and thoroughly mixed.

The granules were compressed to produce tablets each weighing 150 mg.

Tablet formulation

| | Parts/tablet |
|---|---|
| Active compounds | 100 |
| Lactose | 39 |
| Cornstarch (dried) | 80 |
| Gelatin | 4.0 |
| Magnesium stearate | 2.0 |

The method of preparation is identical with that of the preceding, except that 60 parts of starch is used in the granulation process and 20 parts during tableting.

Capsule formulation

| | Parts/capsule |
|---|---|
| Active compounds | 250 |
| Lactose | 150 |

The compounds and lactose were passed through a sieve and the powders well mixed together before filling into hard gelatin capsules of suitable size, so that each capsule contained 400 mg.

Suppositories

| | Parts/suppository |
|---|---|
| Active compounds | 50 |
| Cocoa butter | 950 |

The compounds were powdered and passed through a sieve and triturated with molten cocoa butter at 45° C to form a smooth suspension.

The mixture was well stirred and poured into moulds, each of nominal 1 g. capcity, to produce suppositories.

Cachets

| | Parts/cachet |
|---|---|
| Active compounds | 100 |
| Lactose | 400 |

The compounds were passed through a sieve, mixed with lactose previously sieved and filled into cachets of suitable size so that each contained 500 mg.

| Intramuscular injection (suspension in aqueous vehicle) | |
|---|---|
| | Parts |
| Compounds | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml. | |

The sodium citrate and sodium carboxymethylcellulose were mixed with sufficient water for injection at 90° C. The mixture was cooled to 50° C and the methyl and propyl para-hydroxybenzoates added followed by the medicament previously milled and sieved 300 mesh. When cooled the injection was made up to volume and sterilized by heating in an autoclave.

Having regard to the foregoing disclosure, the following is claimed as the inventive and patentable embodiments thereof:

1. An analgesic composition having a remarkably high analgesic activity, comprising as analgesically active components levopropoxyphene or pharmaceutically acceptable salt thereof and at least one benzodiazepine or pharmaceutically acceptable salt thereof, each in an amount within the weight ratio range of levopropoxyphene-benzodiazepine of from 100:0.5 to 2:1 imparting analgesic activity to the other, neither the levopropoxyphene nor the benzodiazepine when administered separately displaying analgesic activity, the benzodiazepine having the formula:

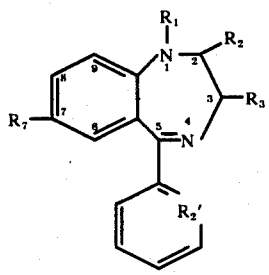

wherein:

$R_1$ is selected from the group consisting of hydrogen, alkyl,

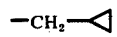

and amino or alkylamino

where R and R' are selected from the group consisting of hydrogen, lower alkyl having from one to three carbon atoms, and bivalent alkylene having from two to four carbon atoms, and linked to the nitrogen at two positions to form a heterocyclic ring;

$R_2$ is selected from the group consisting of hydrogen, oxo oxygen=O, hydroxyl OH, alkyl, and amino or alkylamino

where R and R' are as defined above;

$R_3$ is selected from the group consisting of hydrogen, hydroxyl OH and carboxyl COOH;

$R_7$ is selected from the group consisting of hydrogen, halogen and nitro $NO_2$; and $R_2'$ is selected from the group consistin of

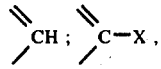

where X is halogen

and amino or alkylamino

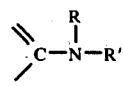

where R and R'' are as defined above.

2. An analgesic composition in accordance with claim 1 in which the benzodiazepine is selected from the group consisting of chlordiazepoxide, diazepam, oxazepam, chlorazepate, flurazepam, lorazepam, nitrazepam, medazepam, bromazepam, and prazepam.

3. An analgesic composition in accordance with claim 1 in which $R_1$ is $CH_3$.

4. An analgesic composition in accordance with claim 1 in which $R_1$ is

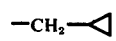

5. An analgesic composition in accordance with claim 1 in which $R_1$ is

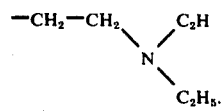

6. An analgesic composition in accordance with claim 1 in which $R_2$ is $NHCH_3$.

7. An analgesic composition in accordance with claim 1 in which $R_2$ is = 0.

8. An analgesic composition in accordance with claim 1 in which $R_2$ is $(OH)_2$.

9. An analgesic composition in accordance with claim 1 in which $R_3$ is OH.

10. An analgesic composition in accordance with claim 1 in which $R_3$ is COOH.

11. An analgesic composition in accordance with claim 1 in which $R_7$ is Cl.

12. Ab analgesic composition in accordance with claim 1 in which $R_7$ is Br.

13. An analgesic composition in accordance with claim 1 in which $R_2'$ is

14. An analgesic composition in accordance with claim 1 in which $R_2'$ is

15. A process for obtaining an analgesic effect, which comprises administering in analgesically effective amount levopropoxyphene or pharmaceutically acceptable salt thereof and at least one benzodiazepine or pharmaceutically acceptable salt thereof, each in an amount within the weight ratio range of levopropoxyphene:benzodiazepine of from 100:0.5 to 2:1 imparting analgesic activity to the other, neither the levopropoxyphene nor the benzodiazepine when administered separately displaying analgesic activity, the benzodiazepine having the formula:

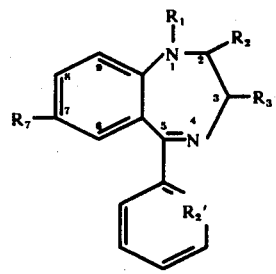

wherein:
$R_1$ is selected from the group consisting of hydrogen, alkyl,

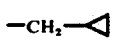

and amino or alkylamino

in which R and R' are selected from the group consisting of hydrogen, lower alkyl having from one to three carbon atoms, and bivalent alkylene having from two to four carbon atoms; and linked to the nitrogen at two positions to form a heterocyclic ring;

$R_2$ is selected from the group consisting of hydrogen, oxo oxygen=O hydroxyl OH, alkyl, and amino or alkylamino

where R and R' are as defined above;
$R_3$ is selected from the group consisting of hydrogen, hydroxyl OH and carboxyl COOH;
$R_7$ is selected from the group consisting of hydrogen, halogen and nitro $NO_2$; and
$R_2'$ is selected from the group consisting of

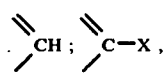

where X is halogen

and amino or alkylamine

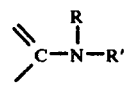

where R and R' are as defined above.

16. A process in accordance with claim 15 in which the benzodiazepine is selected from the group consisting of chlordiazepoxide, diazepam, oxazepam, clorazepate, flurazepam, lorazepam, nitrazepam, medazepam, bromazepam, and prazepam.

17. A pharmaceutical composition in dosage unit form comprising an analgesic composition in accordance with claim 1 and a pharmaceutically acceptable carrier, the dosage unit comprising from about 25 to about 200 mg levopropoxyphene calculated as the free base and from about 0.05 to about 25 mg of the benzodiazepine calculated as the free base.

* * * * *

UNITED STATES PATENT OFFICE
CERTIFICATE OF CORRECTION

Patent No. 4,028,467     Dated  June 7, 1977

Inventor(s)   Frank M. Berger

It is certified that error appears in the above-identified patent and that said Letters Patent are hereby corrected as shown below:

On the Title Page, in the item

[*] Notice: "The portion of the term of this patent subsequent to Apr. 12, 1994, has been disclaimed."

should read -- The portion of the term of this patent subsequent to June 7, 1994, has been disclaimed --.

Signed and Sealed this twenty-third Day of August 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 4,028,467                     Dated June 7, 1977

Inventor(s) Frank M. Berger

It is certified that error appears in the above-identified patent and that said Letters Patent are hereby corrected as shown below:

Column 1, line 32, "d, 1-and $\alpha$, -d-diasterioisomers" should be
--d, 1- and $\alpha$, -d-diastereoisomers--

Columns 3 and 4, Table,

|  | $R_1$ | $R_2$ | $R_3$ | $R_7$ | $R_3'$ |
|---|---|---|---|---|---|
| Chlordiazepoxide | H | NHCH$_3$ | H | Cl | >CH |
| Diazepam | CH$_3$ | =O | H | Cl | >CH |
| Oxazepam | H | =O | OH | Cl | >CH |
| Clorazepate | H | (OH$_2$) | COOH | Cl | >CH |
| Flurazepam | —CH$_2$CH$_2$—N(C$_2$H$_5$)(C$_2$H$_5$) | =O | H | Cl | >CF |
| Lorazepam | H | =O | OH | Cl | >CCl |
| Nitrazepam | H | =O | H | NO$_2$ | >CH |
| Medazepam | CH$_3$ | H | H | Cl | >CH |
| Bromazepam | H | =O | H | Br | >N |
| Prazepam | —CH$_2$—◁ | =O | H | Cl | >CH | should be

UNITED STATES PATENT OFFICE
CERTIFICATE OF CORRECTION

Patent No. 4,028,467　　　　　　　　Dated June 7, 1977

Inventor(s) Frank M. Berger

It is certified that error appears in the above-identified patent and that said Letters Patent are hereby corrected as shown below:

|  | R₁ | R₂ | R₃ | R₇ | R₂' |
|---|---|---|---|---|---|
| Chlordiazepoxide | H | NHCH₃ | H | Cl | >CH |
| Diazepam | CH₃ | =O | H | Cl | >CH |
| Oxazepam | H | =O | OH | Cl | >CH |
| Clorazepate | H | (OH₂) | COOH | Cl | >CH |
| Flurazepam | —CH₂CH₂—N(C₂H₅)(C₂H₅) | =O | H | Cl | >CF |
| Lorazepam | H | =O | OH | Cl | >CCl |
| Nitrazepam | H | =O | H | NO₂ | >CH |
| Medazepam | CH₃ | H | H | Cl | >CH |
| Bromazepam | H | =O | H | Br | >N |
| Prazepam | —CH₂—△ | =O | H | Cl | >CH |

Column 4, line 6, "leveopropoxyphene" should be --levopropoxyphene--

Column 5, line 45, "similer" should be --similar--

Column 10, line 6, "consistin" should be --consisting--

UNITED STATES PATENT OFFICE
CERTIFICATE OF CORRECTION

Patent No. 4,028,467  Dated  June 7, 1977

Inventor(s) Frank M. Berger

It is certified that error appears in the above-identified patent and that said Letters Patent are hereby corrected as shown below:

Column 10, line 55, "=0" should be -- =O --.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*